United States Patent [19]

Foricher et al.

[11] Patent Number: 5,457,219
[45] Date of Patent: Oct. 10, 1995

[54] PHOSPHORUS COMPOUNDS

[75] Inventors: Joseph Foricher, Mulhouse, France; Rudolf Schmid, Arlesheim, Switzerland

[73] Assignee: Hoffmann-La Roche Inc., Nutley, N.J.

[21] Appl. No.: 122,488

[22] PCT Filed: Feb. 1, 1993

[86] PCT No.: PCT/CH93/00026

§ 371 Date: Sep. 27, 1993

§ 102(e) Date: Sep. 27, 1993

[87] PCT Pub. No.: WO93/15091

PCT Pub. Date: Aug. 5, 1993

[30] Foreign Application Priority Data

Jan. 31, 1992 [CH] Switzerland .......................... 00289/92
Apr. 16, 1992 [CH] Switzerland .......................... 01270/92
May 18, 1992 [CH] Switzerland .......................... 01582/92
Jun. 19, 1992 [CH] Switzerland .......................... 01944/92

[51] Int. Cl.$^6$ .................................. C07F 7/08; C07F 9/50
[52] U.S. Cl. ............................................ 556/404; 568/17
[58] Field of Search ................................ 556/404; 568/17

[56] References Cited

U.S. PATENT DOCUMENTS 4,556,740 12/1985 Hansen et al. .
4,956,055 9/1990 Puckette ................................. 568/17 X
5,021,593 6/1991 Nohira et al. .

FOREIGN PATENT DOCUMENTS 104375 4/1984 European Pat. Off. .
398132 11/1990 European Pat. Off. .
92/16535 10/1992 WIPO .

OTHER PUBLICATIONS

Derwent Abstract B05 E11 J04 E19 (1990) for EP 398 132.

Primary Examiner—Paul F. Shaver
Attorney, Agent, or Firm—George M. Gould; George W. Johnston; Robert A. Silverman

[57] ABSTRACT

Novel, racemic and optically active phosphorus compounds of the formula

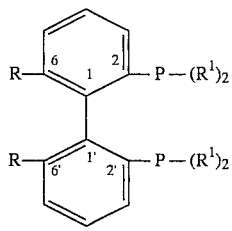

wherein R signifies lower alkyl or lower alkoxy and $R^1$ represents lower alkyl, cycloalkyl or substituted phenyl, are described.

The compounds of formula I are useful in the form of complexes with a metal of Group VIII as catalysts for asymmetric hydrogenations and for enantioselective hydrogen displacements in prochiral allylic systems.

10 Claims, No Drawings

PHOSPHORUS COMPOUNDS

This application is a 371 of PCT/CH 93/00026 Feb. 1, 1993.

The present invention is concerned with novel, racemic and optically active phosphorus compounds of the general formula

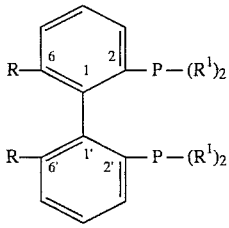

wherein R signifies lower alkyl or lower alkoxy and $R^1$ represents lower alkyl, cycloalkyl or substituted phenyl.

The invention is also concerned with the manufacture of the phosphorus compounds of formula I and with their use for enantioselective reactions such as e.g. asymmetric hydrogenations, enantioselective hydrogen displacements in prochiral, allylic systems, and the like.

The term "lower alkyl" signifies in the scope of the present invention straight-chain or branched alkyl groups with 1 to 5 carbon atoms such as methyl, ethyl, propyl, isopropyl, butyl, isobutyl, tert.butyl, pentyl, isopentyl and the like. The term "lower alkoxy" signifies groups in which the alkyl residue has the foregoing significance. The term "cycloalkyl" signifies three- to five-membered rings such as cyclopropyl, cyclobutyl and cyclopentyl, especially cyclobutyl and cyclopentyl. The term "substituted phenyl" signifies in the scope of the present invention the phenyl residue which can be substituted in the meta- or para-position or which can also be meta, meta-substituted. As substituents there come into consideration phenyl, trialkylsilyl and diphenylalkylsilyl such as trimethylsilyl, triethylsilyl, diphenyl-tert.butylsilyl and the like. Moreover, the term can also signify naphthyl.

The phosphorus compounds of formula I can be present not only in racemic form but also in optically active form. Preferred compounds of formula I are those in which R signifies methoxy or methyl, especially methoxy. Further, there are also preferred those in which $R^1$ signifies isopropyl, isopentyl, cyclopentyl or substituted phenyl. In this case, the phenyl ring is preferably substituted in the para- or meta, meta-position, namely with phenyl, trimethylsilyl or also triethylsilyl. Especially preferred compounds of formula I are:

(R)- or (S)-(6,6'-Dimethoxybiphenyl-2,2'-diyl)bis(di-4-biphenylylphosphine).

(R)- or (S)-(6,6'-Dimethoxybiphenyl-2,2'-diyl)bis[bis-[4-(trimethylsilyl)phenyl]phosphine].

(R)- or (S)-(6,6'-Dimethoxybiphenyl-2,2'-diyl)bis[di-(meta-terphenyl- 5'-yl)phosphine].

(R)- or (S)-(6,6'-Dimethoxybiphenyl-2,2'-diyl)bis[bis(3,5-bis(trimethylsilyl)phenyl)phosphine].

(R)- or (S)-(6,6'-Dimethoxybiphenyl-2,2'-diyl)bis[bis(3,5-bis(triethylsilyl)phenyl)phosphine].

(R)- or (S)-(6,6'-Dimethoxybiphenyl-2,2'-diyl)bis(diisopropylphosphine).

(R)- or (S)-(6,6'-Dimethoxybiphenyl-2,2'-diyl)bis(diethylphosphine).

(R)- or (S)-(6,6'-Dimethoxybiphenyl-2,2'-diyl)bis(dicyclobutylphosphine).

(R)- or (S)-(6,6'-Dimethoxybiphenyl-2,2'-diyl)bis(dicyclopentylphosphine).

The compounds of formula 1 in accordance with the invention can be manufactured in a manner known per se. This can be carried out e.g. starting from compounds of general formula II

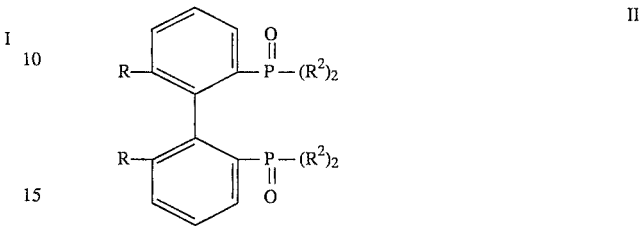

wherein R has the above significance and $R^2$ represents phenoxy, chlorine or bromine.

The manufacture is carried out e.g. by reacting a compound of formula II with a Grignard or lithium compound of the formula $$R^1MgX \text{ or } R^1Li$$

wherein X represents chlorine, bromine or iodine, to give a compound of formula III

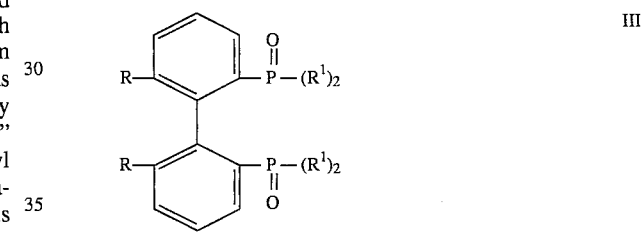

wherein R and $R^1$ have the above significance, which is subsequently reduced to a compound of formula I.

The reaction of a compound of formula II with $R^1MgX$ or $R^1Li$ can be carried out in a manner known per se. This is preferably carried out e.g. under the usual conditions of a Grignard reaction. In this case, compounds of formula II in which $R^2$ represents phenoxy are preferably reacted with a compound of the formula $R^1MgX$ and those in which $R^2$ represents chlorine are preferably reacted with a compound of the formula $R^1$—Li or $R^1MgX$.

The reduction of a compound of formula III, which is racemic or present in the (R)- or (S)-form, can be carried out in a manner known per se. This can be carried out, for example, with silanes such as e.g. trichlorosilane, in an aromatic hydrocarbon, such as, for example, in boiling xylene, or also in acetonitrile etc., conveniently in the presence of an adjuvant base, such as, for example, triethylamine or preferably tributylamine. If desired, this reduction can also be carried out in an autoclave under pressure.

The compounds of formula II which are used as starting materials are known compounds and can be prepared e.g. according to WO 92/16535.

The phosphorus compounds of formula I in accordance with the invention form complexes with transition metals such as, for example, metals of Group VIII especially with ruthenium, rhodium and iridium, which can be used as catalysts in a symmetric hydrogenations and also for enantioselective hydrogen displacements in prochiral, allylic systems. Ruthenium and rhodium complexes are preferred for the aforementioned hydrogenations, while rhodium complexes are preferred for isomerizations. These catalysts, i.e.

the complexes from a metal of Group VIII and the phosphorus compounds of formula I, are novel and are also an object of the present invention.

The aforementioned complexes can be manufactured in a manner known per se, e.g. by reacting a compound of formula I with a compound, which can yield a metal of Group VIII, in a suitable, inert organic or aqueous solvent. As suitable compounds which yield e.g. rhodium there can be mentioned, for example, organic rhodium complexes with ethylene, propylene and the like, as well as with bis-olefins, e.g. (Z,Z)-1,5-cyclooctadiene, 1,5-hexadiene, bicyclo[2.2.1]hepta-2,5-diene, or with other dienes which form readily soluble complexes with rhodium. Preferred compounds which yield rhodium are e.g. di-μ-chloro-bis[η$^4$-(Z,Z)- 1,5-cyclooctadiene]dirhodium(I), di-μ-chloro-bis[η$^4$-norbornadiene]dirhodium(I), di-μ-trifluoroacetato-bis[η$^4$-(Z,Z)-1,5-cyclooctadiene]dirhodium(I), bis[η$^4$-(Z,Z)-1,5-cyclooctadiene]rhodium tetrafluoroborate or bis[η$^4$-(Z,Z)-cyclooctadiene]rhodium perchlorate. Di-μ-chloro-bis[η$^4$-(Z,Z)-1,5-cyclooctadiene]diiridium(I) can be mentioned, for example, as a compound which yields iridium.

The aforementioned rhodium complexes can be represented e.g. by the following formula $$Ru(Z)_2L \qquad \qquad IV$$

wherein Z represents halogen or the group A—COO, A represents lower alkyl, aryl, halogenated lower alkyl or halogenated aryl and L represents a chiral diphosphine ligand of formula I.

These complexes can, in principle, be manufactured in a manner known per se. Conveniently and preferably, ruthenium complexes are manufactured, for example, by reacting a complex of the formula $$[Ru(Z^1)_2L^1{}_m]_p.(H_2O)_q \qquad \qquad V$$

wherein $Z^1$ represents halogen or a group $A^1$—COO, $A^1$ represents lower alkyl or halogenated lower alkyl, $L^1$ represents a neutral ligand, m represents the number 1, 2 or 3, p represents the number 1 or 2 and q represents the number 0 or 1, with a chiral diphosphine ligand of formula I or by reacting a ruthenium complex of the formula $$Ru(CF_3COO)_2L \qquad \qquad VI$$

wherein L represents a chiral diphosphine ligand of formula I, with a salt which yields the anion Z in which Z has the above significance.

The term "neutral ligand" signifies in the scope of the present invention a readily exchangeable ligand such as, for example, a diolefin, e.g. norbornadiene, (Z,Z)-1,5-cyclooctadiene etc., or also a nitrile such as acetonitrile, benzonitrile and the like. Where m represents the number 2 or 3, the ligands can be the same or different.

The ruthenium complexes of formula V are known substances or analogues of known substances which can be obtained readily in a manner analogous to the preparation of the known substances, for example according to Albers, M. O. et al., J. Organomet. Chem. 272, C62–C66 (1984).

The reaction of a ruthenium complex of formula V with a chiral diphosphine ligand of formula I can be carried out in a manner known per se. The reaction can be conveniently carried out in an inert organic solvent. As examples of such solvents there can be mentioned e.g. ethers such as tetrahydrofuran or dioxan, ketones such as, for example, acetone, lower alcohols such as, for example, methanol, ethanol etc., halogenated hydrocarbons such as methylene chloride, chloroform and the like, or also mixtures of such solvents.

Moreover, the reaction can be carried out at a temperature between about 0° C. and about 100° C., preferably between about 15° C. and about 60° C., but with the strict exclusion of oxygen.

The reaction of a ruthenium complex of formula VI (obtainable from a complex of formula V) with a salt which contains the anion Z can be carried out in a manner known per se. The term "a salt which yields the anion Z" signifies in the scope of the present invention, for example, ammonium salts, alkali metal salts or other suitable metal salts. In order to improve the solubility of such salts, crown ethers or the like can also be added in certain instances.

As mentioned earlier, the phosphorus compounds in accordance with the invention in the form of complexes with metals of Group VIII, especially rhodium and ruthenium, can be used, inter alia, for asymmetric hydrogenations. As especially suitable substrates their can be mentioned in this connection particularly allyl alcohols such as e.g. geraniol, 6,7-dihydrogeraniol, 6,7-dihydrofarnesol, 6,7,10,11-tetrahydrofarnesol and the like, enamides such as e.g. (Z)-2-acetyl-1-(p-methoxybenzylidene)-1,2,3,4,5,6,7,8-octahydroisoquinoline, α,β-unsaturated acids such as e.g. 3,4,6,11-tetrahydro-6,11-dioxo-pyridazo[1,2-a]phthalazine-- 1-carboxylic acid as well as functionalized ketones such as β-keto esters, e.g. methyl or ethyl acetoacetate etc., or also 2-pyridyl ketones such as e.g. 2-acetylpyridine, 2-pyridyl 2,8-bis(trifluoromethyl)- 4-quinolyl ketone and the like.

In carrying out such hydrogenations, these complexes can firstly be manufactured and then added to a solution of the substance to be hydrogenated. Alternatively, however, they can also be manufactured in situ, e.g. in the presence of a substance to be hydrogenated.

The asymmetric hydrogenation can be carried out in a suitable solvent which is inert under the reaction conditions. As such solvents there can be mentioned especially aromatic hydrocarbons such as benzene, toluene etc., lower alcohols such as e.g. methanol, water, esters such as ethyl acetate, halogenated hydrocarbons such as methylene chloride, chloroform and the like, cyclic ethers such as tetrahydrofuran or dioxan, and the like, or mixtures of such solvents.

The ratio of metal to ligand L conveniently lies between about 0.05 and about 5 mol or between about 0.5 and about 2 mol, preferably at about 1 mol of metal per mol of ligand. The ratio of metal in the complexes such as e.g. of formula IV to the substances to be hydrogenated conveniently lies between about 0.0005 and about 1 mol %, preferably between about 0.002 and about 0.1 mol %.

The asymmetric hydrogenation with complexes such as e.g. of formula IV is conveniently carried out at a temperature of about 0° C. to about 150° C. depending on the substrate which is used. This hydrogenation is also conveniently carried out under pressure, preferably at a pressure of about 2 to about 200 bar, particularly of about 10 to about 100 bar.

All of the previously mentioned reactions are conveniently carried out under an inert gas such as e.g. argon or nitrogen.

The following Examples serve to illustrate the invention and do not in any manner represent a limitation. In these Examples the selected abbreviations have the following significances:

| TLC | thin-layer chromatography |
| GC | capillar gas chromatography |

-continued

| e.e. | enantiomeric excess. |
| THF | tetrahydrofuran |
| Ar | argon |
| RT | room temperature |

All temperatures are given in °Celsius.

EXAMPLE 1

Synthesis of (R)- and (S)-(6,6'-dimethoxybiphenyl-2,2'-diyl)bis(di- 4-biphenylylphosphine) [(R)- and (S)-p-biphenyl-MeOBIPHEP]

A solution of 4-biphenylylmagnesium bromide, prepared from 3.0 g (123 mmol) of magnesium shavings and 23.3 g (100 mmol) of 4-bromobiphenyl in 250 ml of dry THF, was added dropwise at RT to 6.78 g (10 mmol) of (6,6'-dimethoxybiphenyl-2,2'-diyl)bis(phosphonic acid diphenyl ester). The resulting solution was stirred at RT for a further 30 min. and at 40° for 1 hour and boiled at 65° for 2 hours. After cooling to 0° the reaction mixture was treated slowly with a $NH_4Cl$ solution. The organic phase was separated, washed with sat. NaCl solution, dried over $MgSO_4$, filtered and evaporated. The residue was chromatographed on 500 g of silica gel (elution with ethyl acetate, then $CH_2Cl_2$/ethanol 9:1, then ethanol). The product obtained (8.9 g) was recrystallized from ethyl acetate/hexane. The crystallizate was filtered off under suction, washed with hexane and dried in a HV (~10 Pa) at 100° C. There were obtained 7.0 g of (R)-(6,6'-dimethoxybiphenyl-2,2'-diyl)bis(di-4-biphenylylphosphine oxide) as a white powder; m.p. 190°–210° C.; $[\alpha]_D^{20}=+67.5$ (c=1.0, $CHCl_3$).

5 ml of trichlorosilane were added dropwise under Ar and while cooling to a solution of 6.87 g (7.47 mmol) of (R)-(6,6'-dimethoxybiphenyl- 2,2'-diyl)bis(di-4-biphenylphosphine oxide) in 80 ml of dry xylene and 13 ml of dry tributylamine. The reaction solution was boiled at reflux under Ar for 3 hours. After cooling the reaction mixture was introduced under Ar into 100 ml of deoxygenated 30% NaOH solution via a steel canula, whereby the temperature rose to 60°–70°. The two-phase mixture was stirred at 60°–70° for a further 1 hour and, after cooling, the phases were separated. The organic phase was washed with water (2×100 ml) and with sat. NaCl solution (2×100 ml), dried over $MgSO_4$, filtered and concentrated on a rotary evaporator. The residue was dried at 80° in a HV (~10 Pa) and recrystallized from ethanol/$CH_2Cl_2$. After drying at 100° in a HV (~10 Pa) there were isolated 6.5 g of (R)-(6,6'-dimethoxybiphenyl-2,2'-diyl)bis(di-4-biphenylylphosphine) as a white powder of m.p. 217°–218°; $[\alpha]_D^{20}=+39$ (c=1.0, $CHCl_3$).

The following compounds were manufactured in an analogous manner to the foregoing:

(S)-(6,6'-Dimethoxybiphenyl-2,2'-diyl)bis(di-4-biphenylylphosphine oxide); m.p. 230°–245°; $[\alpha]_D^{20}=+55.8$ (c=1.0, $CHCl_3$).

(S)-(6,6'-Dimethoxybiphenyl-2,2'-diyl)bis(di-4-biphenylylphosphine) [(S)-p-biphenyl-MeOBIPHEP]; m.p. 160°–180°; $[\alpha]_D^{20}=+39.4$ (c=1.0, $CHCl_3$).

(R)-(6,6'-Dimethoxybiphenyl-2,2'-diyl)bis[bis-[4-(trimethylsilyl)phenyl]phosphine oxide]; $[\alpha]_D^{20}=+89.9$ (c=0.8 $CHCl_3$).

(R)-(6,6'-Dimethoxybiphenyl-2,2'-diyl)bis[bis-[4-(trimethylsilyl)phenyl]phosphine] [(R)-p-TMS-MeOBIPHEP]; m.p. 210.7°–211.1°; $[\alpha]_D^{20}=+36.7$ (c=0.8, $CHCl_3$).

EXAMPLE 2

Synthesis of (R)-(6,6'-dimethoxybiphenyl-2,2'-diyl)bis[di(meta-terphenyl- 5'-yl)phosphine] [(R)-3,5-diphenyl-MeOBIPHEP]

A solution of meta-terphenyl-5'-ylmagnesium bromide, prepared from 0.24 g (10 mmol) of magnesium shavings and 2.78 g (9 mmol) of 5'-bromo-meta-terphenyl (Chi-Jen Frank Du, Harold Hart, Kwok-Keung Daniel Ng, J. Org. Chem. 1986, 51, 3162) in 40 ml of dry THF, was allowed to flow at −78° into 0.45 g (1 mmol) of (R)-(6,6'-dimethoxybiphenyl-2,2'diyl)bis(phosphonic acid dichloride). The resulting homogeneous reaction solution was treated dropwise at 0° with a $NH_4Cl$ solution. The organic phase was separated, washed with sat. NaCl solution, dried over $MgSO_4$, filtered and evaporated. The residue was chromatographed on 100 g of silica gel (hexane/ethyl acetate 10%→50%). After drying at 100° in a HV (~10 Pa) there was isolated 0.6 g (50%) of (R)-(6,6'-dimethoxybiphenyl-2,2'-diyl)bis[di-(meta-terphenyl-5'-yl)phosphine oxide ] as a white powder; mp. 181°–205°; $[\alpha]_D^{20}=+42.4$ (c=1.0 $CHCl_3$).

2 ml of trichlorosilane were added dropwise under Ar and while cooling to a solution of 0.5 g (0.4 mmol) of (R)-(6,6'-dimethoxybiphenyl- 2,2'-diyl)bis[di-(meta-terphenyl-5'-yl)phosphine oxide] in dry xylene and 4 ml of dry tributylamine. The reaction solution was boiled at reflux under Ar for 3 hours. After cooling the reaction mixture was introduced under Ar into 50 ml of deoxygenated 30% NaOH via a steel canula, whereby the temperature rose to 60°–70°. The two-phase mixture was stirred at 60°–70° for a further 1 hour and, after cooling, the phases were separated. The organic phase was washed with water (2×50 ml) and with sat. NaCl solution (2×50 ml), dried over $MgSO_4$, filtered and evaporated on a rotary evaporator. After drying at 80° in a HV (~10 Pa) the residue was chromatographed on silica gel (50 g, $CH_2Cl_2$/hexane, then $CH_2Cl_2$). The product obtained was recrystallized from ethanol/$CH_2Cl_2$). After drying at 100° in a HV (~10 Pa) there was isolated 0.4 g of (R)-(6,6'-dimethoxybiphenyl- 2,2'-diyl)bis[di-(meta-terphenyl-5'-yl)phosphine] as a white powder of m.p. 148°–155°; $[\alpha]_H^{20}=-3.5$ (c=1.0, $CHCl_3$).

The following compounds were manufactured in an analogous manner to the foregoing:

(S)-(6,6'-Dimethoxybiphenyl-2,2'-diyl)bis[di-(meta-terphenyl- 5'-yl)phosphine oxide]; m.p. 179°–203° (chromatographed); $[\alpha]_D^{20}=-43.7$ (c=1.0, $CHCl_3$).

(S)-(6,6'-Dimethoxybiphenyl-2,2'-diyl)bis[di-(meta-terphenyl- 5'-yl)phosphine]; m.p. 150°–158° (chromatographed); $[\alpha]_D^{20}=+4.0$ (c=1.0, $CHCl_3$).

EXAMPLE 3

The following compounds can be manufactured in an analogous manner to Example 1 or Example 2:

(R)-(6,6'-Dimethoxybiphenyl-2,2'-diyl)bis[bis-(3,5-bis(trimethylsilyl)phenyl)phosphine oxide]; m.p. 258°–260° (chromatographed); $[\alpha]_D^{20}=+62.4$ (c=1.0, $CHCl_3$) [the 1-bromo-3,5-bis(trimethylsilyl)benzene required for the Grignard reaction was prepared according to B. M. Trost, D. J. Murphy, Organometallics 1985, 4, 1143 ].

(R)-(6,6'-Dimethoxybiphenyl-2,2'-diyl)bis[bis-(3,5-bis(trimethylsilyl)phenyl)phosphine] [(R)-3,5-TMS-MeOBIPHEP]; m.p. 207°–209°; $[\alpha]_D^{20}=+19.7$ (c=1.0, $CHCl_3$).

(S)-(6,6'-Dimethoxybiphenyl-2,2'-diyl)bis[bis-(3,5-bis(t- rimethylsilyl)phenyl)phosphine oxide]; m.p. 258°–260° (chromatographed); $[\alpha]_D^{20}=-62.4$ (c=1.0, CHCl$_3$).

(S)-(6,6-Dimethoxybiphenyl-2,2'-diyl)bis[bis-(3,5-bis(trimethylsilyl)phenyl)phosphine] [(S)-3,5-TMS-MeO-BIPHEP]; m.p. 209°–209°; $[\alpha]_D^{20}=-19.2$ (c=1.0, CHCl$_3$).

(R)-(6,6'-Dimethoxybiphenyl-2,2'-diyl)bis[bis-(3,5-bis-(triethylsilyl)phenyl)phosphine oxide]; $[\alpha]_D^{20}=+31.0$ (c=1.0, CHCl$_3$).

(R)-(6,6'-Dimethoxybiphenyl-2,2'-diyl)bis[bis-(3,5-bis-(triethylsilyl)phenyl)phosphine]; m.p. 58°–59°; $[\alpha_D^{20}=-18.1$ (c=1.0, CHCl$_3$).

(S)-(6,6'-Dimethoxybiphenlyl-2,2'-diyl)bis[bis-(3,5-bis-(triethylsilyl)phenyl)phosphine oxide]; $[\alpha]_D^{20}=-30$ (c=10 CHCl$_3$).

(S)-(6,6'-Dimethoxybiphenyl-2,2'-diyl)bis[bis-(3,5-bis-(triethylsilyl)phenyl)phosphine]; m.p. 58°–59°; $[\alpha]_D^{20}=+16.5$ (c=1.0, CHCl$_3$).

(S)-(6,6'-Dimethoxybiphenyl-2,2'-diyl)bis(diisopropylphosphine oxide); m.p. 194.5°–196.5°; $[\alpha]_D^{20}=-61.3°$ (c=1.0, CHCl$_3$).

(S)-(6,6'-Dimethoxybiphenyl-2,2'-diyl)bis(diisopropylphosphine); m.p. 138°–140°; $[\alpha]_D^{20}=-18.4°$ (c=1.0, CHCl$_3$).

(R)-(6,6'-Dimethoxybiphenyl-2,2'-diyl)bis(diisopropylphosphine oxide); m.p. 195°–196°; $[\alpha]_D^{20}=+62°$ (c=1.0, CHCl$_3$).

(R)-(6,6'-Dimethoxybiphenyl-2,2'-diyl)bis(diisopropylphosphine); mp. 140°–141°; $[\alpha]_D^{20}=+19.7°$ (c=1.0, CHCl$_3$).

(RS)-(6,6'-Dimethoxybiphenyl-2,2'-diyl)bis(diethylphosphine oxide); m.p. 255°–256°.

(RS)-(6,6'-Dimethoxybiphenyl-2,2'-diyl)bis(diethylphosphine); m.p. 137°.

(R)-(6,6'-Dimethoxybiphenyl-2,2'-diyl)bis(dicyclobutylphosphine oxide); m p. 239°–242°; $[\alpha]_D^{20}=+7.0$ (c=1.0, CHCl$_3$).

(R)-(6,6'-Dimethoxybiphenyl-2,2'-diyl)bis(dicyclobutylphosphine); m.p. 172°–175°; $[\alpha]_D^{20}=+3.2$ (c=1.0, CHCl$_3$).

(S)-(6,6'-Dimethoxybiphenyl-2,2'-diyl)bis(dicyclobutylphosphine oxide); mp. 239°–242°; $[\alpha]_D^{20}=-6.4$ (c=1.0 CHCl$_3$).

(S)-(6,6'-Dimethoxybiphenyl-2,2'-diyl)bis(dicyclobutylphosphine); m.p. 173°–174°; $[\alpha]_D^{20}=-2.1$ (c=1.0, CHCl$_3$).

(R)-(6,6'-Dimethoxybiphenyl-2,2'-diyl)bis(dicyclopentylphosphine oxide); m.p. 287°–288°; $[\alpha]_D^{20}=+5.3$ (c=1.0, CHCl$_3$).

(R)-(6,6'-Dimethoxybiphenyl-2,2'-diyl)bis(dicyclopentylphosphine); m.p 161°–163°; $[\alpha]_D^{20}=-15.1$ (c=10 CHCl$_3$).

(S)-(6,6'-Dimethoxybiphenyl-2,2'-diyl)bis(dicyclopentylphosphine oxide); m.p. 287°–288°; $[\alpha]_D^{20}=-5.6$ (c=1.0, CHCl$_3$).

(S)-(6,6'-Dimethoxybiphenyl-2,2'-diyl)bis(dicyclopentylphosphine); m.p. 160°–161°, $[\alpha]_D^{20}=+15.0$ (c=1.0, CHCl$_3$).

EXAMPLE 4 a) 2.06 mg (0.0063 mmol) of di($\eta^2$-acetato)-($\eta^4$-cycloocta- 1,5-diene)ruthenium(11) [B. Heiser et al., Tetrahedron: Asymmetry 2, 51 (1991)] and 5.6 mg (0.0063 mmol) of (R)-p-biphenyl-MeOBIPHEP (prepared according to Example 1) were stirred in 0.7 ml of tetrahydrofuran and 2 ml of ether at 40° for 16 hours in a glove box (<1 ppm oxygen) to give a yellow, clear catalyst solution.

b) A 500 ml autoclave was loaded in a glove box with 15.0 g (50.4 mmol) of (Z)-2-acetyl-1-(p-methoxybenzylidene)-1,2,3,4,5,6,7,8-octahydroisoquinoline, 170 ml of methanol and the catalyst solution prepared according to a). The hydrogenation was carried out at 100° and 35 bar for 22 hours. The conversion was 98.5%. A 2 g product-containing aliquot of the hydrogenation solution was evaporated and the residue was dissolved in diethyl ether. The ether solution was filtered through a silica gel pad in order to separate the catalyst. Evaporation of the filtrate gave 1.97 g of (S)-2-acetyl-1-(p-methoxybenzyl)-1,2,3,4,5,6,7,8-octahydroisoquinoline as yellowish crystals of 95.9% e.e.

In order to determine the e.e. value, the product was hydrolyzed at 170° for 18 hours in a mixture of ethylene glycol and 40% aqueous potassium hydroxide solution. The amine formed was converted with (o)-camphanoyl chloride in pyridine/4-dimethylaminopyridine into the mixture of diastereomeric amides and the latter was analyzed by GC.

EXAMPLE 5

A catalyst with (R)-p-TMS-MeOBIPHEP (prepared according to Example 1) as the ligand was prepared in an analogous manner to Example 4 and the hydrogenation was also carried out in an analogous manner: 94% conversion, 96% e.e.

EXAMPLE 6

10.14 mg (0.031 mmol) of di($\eta^2$-acetato)-($\eta^4$-cycloocta-1,5-diene)ruthenium(II) [B. Heiser et al., Tetrahedron: Asymmetry 2, 51 (1991)]and 13.83 mg (0.031 mmol) of [(S)-6,6'-dimethoxybiphenyl- 2,2'-diyl]bis[diisopropylphosphine] (prepared according to Example 3) were dissolved in 6 ml of ether and 2 ml of THF in a 50 ml Schlenk tube in a glove box (O$_2$ content<1 ppm) and stirred at 40° for 1.5 hours. A red, clear catalyst solution formed. The hydrogenation was carried out in a 500 ml autoclave loaded with 8.0 g (31.0 mmol) of 3,4,6,11-tetrahydro-6,11-dioxo-pyridazo[1,2-a]phthalazine-1-carboxylic acid, 3.14 g (31.0 mmol) of triethylamine, 150 ml of methanol and the catalyst solution prepared above. The hydrogenation was carried out at 60°, a constant pressure of 40 bar of pure hydrogen and while stirring intensively. After 5 hours the conversion was 99.9% according to GC. The yellow hydrogenation solution was evaporated to a weight of 25 g at 50°/220 mbar on a rotary evaporator. 4.42 ml of 25 percent HCl solution and subsequently 27 ml of water were added dropwise to the residual solution while stirring at 20°–35°. The suspension was stirred at 20° for 1 hour and at 0° for 1 hour. After filtration and drying there were obtained 7.7 g (96%) of (S)-1,2,3,4,6,11-hexahydro-6,11-dioxopyridazo[1,2-b]phthalazine-1-carboxylic acid as almost white crystals with an enantiomeric purity of 96.5% e.e. The e.e. value was determined by HPLC on an α-APG column.

We claim:

1. A racemic and optically active phosphorous compound of the formula

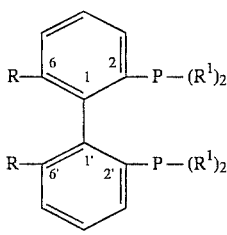

wherein

R is lower alkyl or lower alkoxyl; and $R^1$ is a straight-chain or branched alkyl group with 1 to 5 carbon atoms; cycloalkyl having three to five ring members; phenyl substituted in the meta- or para-position or meta, meta-substituted, wherein the substituents are selected from the group consisting of phenyl, trialkylsilyl and diphenylalkylsilyl; or naphthyl.

2. Racemic and optically active phosphorus compounds of formula I according to claim 1, wherein R represents methoxy.

3. Racemic and optically active phosphorus compounds of formula I according to claim 1, wherein $R^1$ represents isopropyl, isopentyl, cyclopentyl or substituted phenyl.

4. A compound of formula I according to claim 1, the compound being (R)- or (S)-(6,6'-Dimethoxybiphenyl-2,2'-diyl)bis(di- 4-biphenylylphosphine).

5. A compound of formula I according to claim 1, the compound being (R)- or (S)-(6,6'-Dimethoxybiphenyl-2,2'-diyl)bis[ bis-[4-(trimethylsilyl)phenyl]phosphine].

6. A compound of formula I according to claim 1, the compound being (R)- or (S)-(6,6'-Dimethoxybiphenyl-2,2'-diyl)bis[ di-(meta-terphenyl-5'-yl)phosphine].

7. A compound of formula I according to claim 1, the compound being (R)- or (S)-(6,6'-Dimethoxybiphenyl-2,2'-diyl)bis[bis-[3,5-bis(trimethylsilyl)phenyl]phosphine].

8. A compound of formula I according to claim 1, the compound being (R)- or (S)-(6,6'-Dimethoxybiphenyl-2,2'-diyl)bis(diiso-propylphosphine).

9. A compound of formula I according to claim 1, the compounds being (R)- or (S)-(6,6'-Dimethoxybiphenyl-2,2'-diyl)bis-(dicyclopentylphosphine).

10. Racemic and optically active phosphorous compounds of formula I according to claim 2 wherein $R^1$ represents isopropyl, isopentyl, cyclopentyl or substituted phenyl.

* * * * *